United States Patent [19]

Mirviss

[11] Patent Number: 4,650,876
[45] Date of Patent: Mar. 17, 1987

[54] HYDROGENATION OF SUBSTITUTED, UNSATURATED HYDANTOINS TO SUBSTITUTED, SATURATED HYDANTOINS

[75] Inventor: Stanley B. Mirviss, Stamford, Conn.

[73] Assignee: Stauffer Chemical Company, Westport, Conn.

[21] Appl. No.: 804,216

[22] Filed: Dec. 3, 1985

Related U.S. Application Data

[63] Continuation-in-part of Ser. No. 641,886, Aug. 17, 1984, abandoned.

[51] Int. Cl.$^4$ ............................................. C07D 233/74
[52] U.S. Cl. ................................... 548/308; 548/311; 548/312; 548/313; 548/314
[58] Field of Search ............... 548/308, 311, 312, 313, 548/314

[56] References Cited

U.S. PATENT DOCUMENTS

| | | | |
|---|---|---|---|
| 1,628,190 | 5/1927 | Raney | 75/119 |
| 1,915,473 | 6/1933 | Raney | 502/301 |
| 2,479,065 | 8/1949 | Gresham et al. | 548/308 |
| 2,557,920 | 6/1951 | White | 548/499 |
| 2,605,282 | 7/1952 | Britton et al. | 562/446 |
| 2,642,459 | 6/1953 | White | 562/575 |

OTHER PUBLICATIONS

House, H., *Modern Synthetic Reactions*, 2nd ed., Benjamin/Cummings, Menlo Park, Calif., 1972, pp. 6–7.
Elks, J., et al., *J. Chem. Soc.*, 629 (1944).
Doyle, F., et al., *J. Chem. Soc.*, 2265 (1955).
Covert, L. et al. *J. Amer. Chem. Soc.* 54, 4116 (1932).
Raney, M., *Ind. and Eng. Chem.* 33, 1199 (1940).
Borrows, E., et al. *J. Chem. Soc.* 1949, 5185.
Hahn, D., et al., *J. Amer. Chem. Soc.* 47, 2941 (1925).
Miller, E., et al. *J. Chem. Soc.* 1938, 1910.
Ware, E., *Chem. Rev.* 46, 403, 431–436 (1950).
Freifelder, M., *Practical Catalytic Hydrogenation*, Wiley–Interscience, New York, 1971, p. 8.

*Primary Examiner*—Richard A. Schwartz
*Attorney, Agent, or Firm*—Paul J. Juettner

[57] ABSTRACT

Unsaturated hydantoins are reduced to the corresponding saturated hydantoin by carrying out the hydrogenation reaction using a nickel catalyst in the presence of more than a stoichiometric amount of caustic. Use of this process allows for almost complete hydrogenation in short reaction times and also allows the reaction to be done using aqueous solvents and low levels of catalyst.

Frothing or foaming of the hydrogenation reaction mixture at elevated concentrations of hydantoin is overcome by incremental addition of hydantoin to the hydrogenation reaction mixture.

9 Claims, No Drawings

HYDROGENATION OF SUBSTITUTED, UNSATURATED HYDANTOINS TO SUBSTITUTED, SATURATED HYDANTOINS

CROSS REFERENCE TO RELATED APPLICATION

The present application is a continuation-in-part of application Ser. No. 641,886, filed Aug. 17, 1984, now abandoned.

FIELD OF THE INVENTION

The present invention relates to a novel process for the hydrogenation of substituted unsaturated hydantoins to substituted, saturated hydantoins. More particularly, this invention relates to a novel process for the hydrogenation of unsaturated hydantoins which uses inexpensive catalysts, does not require high pressure, can be carried out in aqueous solvents, and which results in substantially complete hydrogenation of the unsaturated hydantoin in short reaction times using low levels of catalyst.

BACKGROUND OF THE INVENTION

Unsaturated hydantoins are important precursors in the synthesis of some amino acids. These unsaturated hydantoins can be formed by any number of reactions with one of the more commonly used being a condensation reaction between an aldehyde and a substituted or unsubstituted hydantoin. In this reaction, an ethylenic bond is formed between the non-carbonyl, or C-5, carbon of the hydantoin moiety and the carbonyl carbon of the original aldehyde. Further reduction, or hydrogenation, of this ethylenic linkage is a necessary step in the synthesis of some amino acids. This step must be done without hydrogenation of any of the aromatic or aliphatic substituents of the hydantoin moiety other than at this ethylenic linkage. Previously, this hydrogenation step has been done using hydrogen and a nickel catalyst under high pressure or by using hydrogen and a very expensive noble metal catalyst such as palladium or platinum under little or no pressure.

The use of one or more of these techniques is reported in a number of U.S. patents. In U.S. Pat. No. 2,605,282, 5-vanillylidenehydantoin is reduced to the 5-vanillylhydantoin by dissolving the unsaturated hydantoin in an aqueous solution containing 4 to 10 percent by weight of sodium hydroxide (75 mole percent of the unsaturated hydantoin) and shaking the mixture with hydrogen under pressure in the presence of a palladium containing hydrogenation catalyst. The reduction is carried out at a temperature of 25° to 40° C. at a pressure of 60 pounds per square-inch gauge or higher for 1 to 4 hours.

In U.S. Pat. No. 2,479,065, 5-benzalhydantoin is reduced to 5-benzylhydantoin using a caustic activated nickel aluminum alloy catalyst, methanol as a solvent and pressures of from 750 to 760 atmospheres. One disadvantage of the above method is the use of extremely high pressures to complete the hydrogenation in a short reaction time. The above mentioned patent does not specifically define the type of nickel aluminum alloy to be caustic activated or the degree of caustic activation. Although nickel aluminum alloys are commonly employed catalysts in hydrogenation procedures, a distinction must be drawn between a nickel alloy catalyst and a particular class of nickel type catalyst called Raney nickel catalyst. The accepted method of making the latter catalyst involves reacting the nickelaluminum alloy with caustic to remove the aluminum and then washing the precipitated nickel with water to remove essentially all the caustic to produce a spongy nickel catalyst. [Ind. and Eng. Chem. 33 1199 (1940)]: Hereinafter, the term Raney nickel catalyst refers to the form of nickel catalyst produced by the above procedure.

Prior work on the process of low-pressure hydrogenation of unsaturated hydantoins as disclosed in the parent application, Ser. No. 641,886, was done at a 10 percent concentration in water. Engineering studies indicated a large savings in production costs could be achieved by increasing the concentration to 20 percent. However, at 20 percent concentration level, severe frothing and foaming occurs at the upper level of the liquid phase with the hydrogen gas. This pasty froth expands and fills up all the free space in the reaction vessel and even into accessory equipment. The frothing occurs regardless of the scale of the reaction. The reduction in agitation speed or the increase in reaction vessel and reaction size (from 250 milliliter to 22 liter flasks), or the use of baffles, or the use of surface active agents does not overcome the problem. The use of a cylindrical reaction vessel in place of the spherical laboratory reaction flask is of some assistance in overcoming the problem. The use of a stoichiometric amount of sodium hydroxide (100 mole percent) and increased reaction temperature has also been attempted. None of these changes eliminates the frothing problem.

SUMMARY OF THE INVENTION

In accordance with the present invention, an unsaturated hydantoin is reduced to the corresponding saturated hydantoin by carrying out the hydrogenation step using Raney nickel catalyst in the presence of more than a stoichiometric amount of caustic. Using this method, it is possible to obtain high yields of the saturated hydantoin in short reaction times using low levels of catalyst. In addition the reaction can be carried out at atmospheric pressures using aqueous solvents.

It has also been found that the severe frothing and foaming problem encountered during hydrogenation using an unsaturated hydantoin in elevated amounts can be overcome by incrementally adding the unsaturated hydantoin to the hydrogenation liquid medium. This process step allows the reaction to be run at a more concentrated level on a large scale to improve the economics of the reaction.

DETAILED DESCRIPTION OF THE INVENTION

The process of the invention is particularly suited for the reduction of substituted unsaturated hydantoins of the general formula.

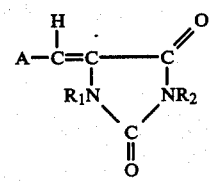

where A is X or Y, and X is an unbranched or branched alkyl or alkenyl group, a cycloalkyl group, a cycloalkenyl group, an alkylthio group, a haloalkyl group, a haloalkenyl group, a hydroxyalkyl group, an aralkyl group, a mono- or dialkylaminoalkyl group, an acylaminoalkyl group, or a mercaptoalkyl group. Preferably the alkyl groups contain 1 to about 20, especially 1 to about 10 carbon atoms, the alkenyl group 1 to about 10, especially 1 to about 5 carbon atoms, the cycloalkyl and cycloalkenyl groups from about 3 to about 15, preferably from about 3 to about 10 carbon atoms. In a given case in the cycloalkyl or cycloalkenyl group, one or more —CH$_2$— units can also be replaced by —O—, —S—, or —NH—, or —C= can be replaced by —N= so that there is present the corresponding heterocyclic ring with 3 to about 15, preferably from about 3 to about 10 ring atoms. The alkoxy, alkylthio, hydroxyalkyl, mercaptoalkyl, mono or dialkylaminoalkyl and acylaminoalkyl groups contain preferably 1 to about 10, especially 1 to about 6 carbon atoms in the alkyl or acyl groups, and Y is

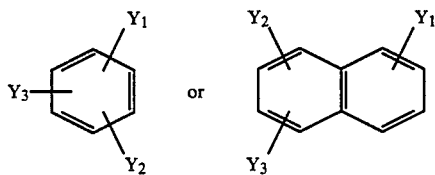

in which Y$_1$, Y$_2$, and Y$_3$ are the same or different and can be X as defined above, hydrogen, halogen, e.g. of atomic weight 9 to 80, a hydroxy group, a nitro group, a cyano group, an amino group, an aryl group, an alkoxy group, an acyloxy group, an aralkyl group, or an alkaryl group. Preferably, the aralkyl and the alkaryl groups contain from about 7 to about 15 carbons in the alkylene or alkyl groups. In a given case, two of the groups Y$_1$ to Y$_3$ together can form an alkylene or alkenylene group with from about 3 to about 5 carbon atoms whereby in this case one or more —CH$_2$— units can be replaced by —O—, —S—, or —NH— or —CH= can be replaced by —N=.

R$_1$ and R$_2$ are the same or different and are hydrogen, alkyl, aryl, acyl, or amino.

The unsaturated hydantoin to be reduced can be purchased commercially or can be synthesized, for example, through the condensation reaction of an aliphatic or aromatic aldehyde with a substituted or unsubstituted hydantoin.

One such condensation reaction is disclosed in my copending application No. 641,888 entitled "New Inexpensive Catalyst for Synthesis of Unsaturated Hydantoins", in which the condensation reaction of an aldehyde and hydantoin is carried out in the presence of a basic salt of an inorganic acid. In this process, representative aldehydes which may be used include, but are not limited to, aliphatic aldehydes such as butyraldehyde, isobutyraldehyde, valeraldehyde, isovaleraldehyde, caproaldehyde, enanthaldehyde, nonaldehyde, cyclobutylaldehyde, cyclopentylaldehyde, cyclohexylaldehyde, furfural, 2-thiophenealdehyde, 2-pyrrolealdehyde, imidazolealdehyde, oxazolealdehyde, 3-indolealdehyde, pyridylaldehyde, pyrimidylaldehyde, malonic acid half aldehyde, as well as the monoaldehyde derivatives of dicarboxylic acids such as, for example, succinic, oxalic, glutaric and adipic acid.

Aromatic aldehydes can also be used. Examples of aromatic aldehydes include, but are not limited to, benzaldehyde, tolylaldehyde, 4-isopropylbenzaldehyde, 4-hydroxybenzaldehyde, 3,4,5-trimethoxybenzaldehyde, 3-bromo-4-methoxybenzaldehyde, 3,4-methylenedioxybenzaldehyde, 2-hydroxy-4-nitrobenzaldehyde, 4,5-dimethoxy-2-nitrobenzaldehyde, salicylaldehyde, vanillin, 4-phenylbenzaldehyde, 4-benzylbenzaldehyde, 4-fluorobenzaldehyde, 4-dimethylaminobenzaldehyde, 4-acetoxybenzaldehyde, 4-acetaminobenzaldehyde, 4-methylthiobenzaldehyde, and 3,5-dichloro-4-hydroxybenzaldehyde. Additional aldehydes include p-tolylaldehyde, m-tolylaldehyde, 4-chlorobenzaldehyde, 4-hexylbenzaldehyde, 2-allylbenzaldehyde, 4-allylbenzaldehyde, 2-vinylbenzaldehyde, 3-vinylbenzaldehyde, 4-methallylbenzaldehyde, 4-crotylbenzaldehyde, 2-nitrobenzaldehyde, 3-nitrobenzaldehyde, 4-nitrobenzaldehyde, 2-aminobenzaldehyde, 4-aminobenzaldehyde, 4-cyclopropylbenzaldehyde, 2-cyclopropylbenzaldehyde, 4-cyclohexylbenzaldehyde, 2,6-dichlorobenzaldehyde, anisaldehyde, 3-hydroxybenazaldehyde, 2-hydroxybenzaldehyde, 2-hydroxy-4-methylbenzaldehyde, 2-hydroxy-3-methoxybenzaldehyde, veratraldehyde, 2,4-dihydroxybenzaldehyde, 2,5-dihydroxybenzaldehyde, 4-cyclohexenylbenzaldehyde, 4-cyclooctylbenzaldehyde, 4-piperidinylbenzaldehyde, 4-pyridinebenzaldehyde, 4-furylbenzaldehyde, 4-thienylbenzaldehyde, 4-phenylethylbenzaldehyde, 4-sec.butylbenzaldehyde, 4-morpholinobenzaldehyde, 4-isopropoxybenzaldehyde, 2-propoxybenzaldehyde, 3-ethoxybenzaldehyde, 4-hexoxybenzaldehyde, 2-isopropylaminobenzaldehyde, 4-hexylaminobenzaldehyde, 4-diethylaminobenzaldehyde, 4-dipropylaminobenzaldehyde, 4-methylethylaminobenzaldehyde, 3,4-ethylenedioxybenzaldehyde, 4-acetylthiobenzaldehyde, 4-propionoxybenzaldehyde, 4-formoxybenzaldehyde, 4-butyroxybenzaldehyde, 3,4-tetramethylenebenzaldehyde, 3,4-trimethylenebenzaldehyde, 3,4-dihydroxybenzaldehyde, alphanapthaldehyde, betanapthaldehyde, and 3-indenecarboxyaldehyde.

In addition, the above process is also suited to the condensation reaction of hydantoins substituted at the N-1 and N-3 position such as 3-methylhydantoin, 1,3-diacetylhydantoin, 1,3-diphenylhydantoin, 3-benzylhdantoin, 1,3-dibenzylhydantoin and the like.

It has now been discovered that the unsaturated hydantoin produced in the above reaction, available commercially or produced through other means, can be reduced at a fast reaction time with little or no pressure to the corresponding saturated hydantoin by carrying out the hydrogenation step using a Raney nickel catalyst in the presence of more than a stoichiometric amount of caustic.

The Raney nickel catalyst employed is available commercially (Davison Division of W. R. Grace). Briefly, the preparation of this catalyst involves fusing about 50 parts nickel with about 50 parts aluminum as described in U.S. Pat. Nos. 1,628,190 and 1,915,473, pulverizing the alloy and dissolving out most of the aluminum with sodium hydroxide solution [J. Am. Chem. Soc. 54, 4116 (1932)]. The nickel is then washed to remove any residual sodium hydroxide [Ind. and Eng. Chem. 33 1199 (1940)]. The exact mechanism through which Raney nickel exerts its catalytic activity is not known. Various theories have been put forth including absorbed hydrogen or the formation of a nickel hydride. A complete discussion of this subject can be found in Freifelder, *Practical Catalytic Hydrogenation*, Wiley Interscience, 1971 pp. 6–7, the discussion therein being incorporated by reference. As is known to those skilled in the art, the Raney nickel catalyst must be kept under water.

The hydrogenation reaction of the present invention is carried out in the presence of an effective amount of Raney nickel catalyst ranging from about 0.1 to about 50, preferably from about 0.3 or from about 1.0 to about 40 percent by weight of the unsaturated hydantoin.

An effective amount of solid or liquid caustic of any strength from 10–100 percent by weight, ranging from about 100 to about 300, preferably from about 105 to about 250, with optimum results at about 105 to about 200 mole percent, based on the amount of unsaturated hydantoin, is also added to the reaction mixture. The strength of the caustic solution produced can range from 0.1 to 15 weight percent (0.1N–2.5N) based on the amount of water used. Preferably the process would comprise using a reaction mixture containing from about 0.5 to about 10 weight percent sodium hydroxide. Other caustics, such as the hydroxide derivative of lithium, potassium, etc. may also be used.

The unsaturated hydantoin can be dissolved and added as a solvent solution or added as a solid. The preferred reaction medium is water due to cost and the fact that the reaction product is highly soluble in water. Since the unsaturated hydantoins are, for the most part, insoluble in water, they are preferably added to the reaction mixture as solids. The amount of solids in the reaction mixture contributed by the unsaturated hydantoin will reduce as the reaction proceeds as the reaction product is soluble in water. There is no critical threshold amount of unsaturated hydantoin needed to effect hydrogenation. As the level of unsaturated hydantoin increases relative to the amount of water, frothing and foaming can occur. For example, at 10 percent benzalhydantoin, minimum and inconsequential foaming has been encountered. At 20 percent unsaturated hydantoin, frothing and foaming is prevalent. It has been found that the frothing and foaming of the reaction can be overcome by the use of incremental or sequential addition of the unsaturated hydantoin to the aqueous hydrogenation reaction system containing the Raney nickel catalyst and the caustic. Since the preferred reaction medium is water, and since the unsaturated hydantoin is insoluble in water, it is preferred to add the unsaturated hydantoin in fractional amounts of the hydantoin charge at any one time. The fractional amount that can be used is any amount up to that amount which can be added to the reaction mixture at any one time to produce a reaction mass which does not exhibit substantial foaming or frothing. Preferably, fractional amounts ranging up to about ½ the unsaturated hydantoin charged to the reaction can be used. The actual percentage may vary depending on the reactants and reaction conditions. Amounts can be easily adjusted by a person of ordinary skill in the art. The time interval between additions should be such as to allow reaction and hence dissolution of at least 10 percent of the unsaturated hydantoin solid in the reaction mass. Generally, reaction can be observed by a reduction in the usual solids in the reaction mixture. Times between fractional additions can range from a low of about 15 minutes to a high of 1 hour or more. As one of the preferred embodiments, ½ charges can be made with an interval of 1 hour.

Hydrogen is bubbled in with vigorous stirring. The reaction can be performed at atmospheric or elevated pressures. The higher the pressure, the faster the reaction rate but preferably, the reaction is run at a pressure of 0 to about 100 psig.

The temperature at which the reaction is run can range from 0° to about 100° C., preferably from about 10° to about 65° C. with optimum results being seen at from about 25° C. to about 40° C.

The vessel in which the reaction is carried out in the laboratory may be a round bottom flask, a pressure resistant glass bottle, a Parr pressure bottle, a resin flask (bottle), a Morton flask, etc. The reaction may be performed in a batch fashion or a continuous fashion.

When the reactants are introduced, the reaction can be summarized as follows:

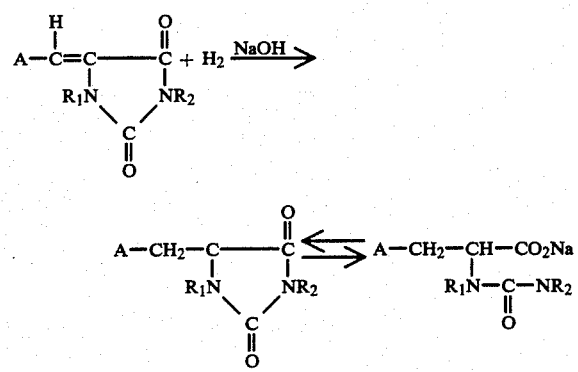

in which it is to be noted that an equilibrium exists between product I, the saturated hydantoin, and product II, the sodium salt of the ring opened saturated hydantoin. Product II can also be called a sodium salt of an N-carbamyl, beta-substituted alanyl derivative. Either or both products are desirable since the process is designed to hydrogenate the ethylenic linkage between a methine carbon of the aliphatic, aromatic or heterocyclic substituent on the hydantoin moiety and the non-carbonyl carbon of the hydantoin moiety or its original derivative. Accordingly, the amount of either compound I and/or compound II may be measured by conventional methods, including liquid chromatography, melting point, UV analysis, etc.

The process of the invention can comprise, consist of, or consist essentially of the following examples:

EXAMPLE 1

20 Wt% Raney Nickel (Based on Benzalhydantoin) 80 Psig, 25° C., No NaOH

A 250-ml pressure resistant glass bottle was charged with 5 g. of 5-benzalhydantoin, 150 ml of methanol, and 1 g. (20 wt %) of No. 2800 Raney Nickel (Davison Div.—W. R. Grace). The bottle was pressurized to 45 pounds per square inch gauge, (psig.) with $H_2$ and shaken on a Parr apparatus. When the pressure dropped to 35 psig., the bottle was repressured to 45 psig. for an average pressure of 40 psig. The reaction was followed by periodic sampling and UV analysis. After 25 hours, the reaction was 37 percent complete; at 49 hours, 75 percent complete; at 53.5 hours, 91 percent complete. The product was essentially all 5-benzylhydantoin.

EXAMPLE 2

30 Wt% Raney Nickel (Based on Benzalhydantoin) 0 Psig (ATM Pressure), 25° C. No NaOH A 250 ml round bottom flask, fitted with a stirrer, dip tube, thermometer, and condenser, was charged with 5 g of 5-benzalhydantoin, 150 ml of methanol and 1.5 g (30 wt %) of No. 2800 Raney Nickel (Davison Div.—W. R. Grace). Hydrogen was bubbled in with vigorous stirring. After 45 hours, the $H_2$ flow was stopped and the hydrogenation product was filtered to remove the catalyst. Analysis of the filtrates by UV showed that the hydrogenation was 94 percent complete. The filtrate was evaporated to dryness and a white solid was isolated which had a melting point of 180° C. to 182.5° C. The literature shows a melting point of 188° C.–190° C. Liquid chromatographic analysis showed the product to be over 95 percent pure 5-benzylhydantoin.

EXAMPLE 3

20 Wt % Raney Nickel 0 Psig, 40° C., 100 Mole % NaOH (Based on Weight of Benzalhydantoin)

Similar to Example 2, except 75 ml of water and 75 ml of methanol were used as diluent. 1.2 g of NaOH (100 mole percent based on benzalhydantoin) and 1 g of No. 2800 Raney Nickel (Davison Div.—W. R. Grace) were used. The hydrogen was bubbled in with vigorous stirring. The temperature was held at approximately 40° C. After 7 hours of stirring, the hydrogenation, as measured by UV analysis, was 42 percent complete; at 14 hours, 64 percent complete, at 23 hours, 95 percent complete. Liquid chromatographic analysis showed the reaction to be 96-98 percent complete. The product consisted of 21 percent 5-benzylhydantoin, 71 percent N-carbamylphenylalanine, 2 percent phenylalanine and 4 percent unreacted 5-benzalhydantoin. All were present as sodium salts.

EXAMPLE 4

20 Wt % Raney Nickel 0 Psig, 25°-35° C., Distilled Water and 113 Mole % NaOH Similar to Example 3, 5 g of 5-benzalhydantoin, 150 ml of distilled water as diluent, 1.4 g of NaOH (113 percent mole percent of benzalhydantoin) and 1.0 g of No. 2800 Raney Nickel (Davison Div.—W. R. Grace) were added to the reaction mixture. After 8 hours of hydrogen addition with stirring, the material showed over 95 percent complete hydrogenation by UV analysis and 100 percent completion as measured by liquid chromatography analysis. The product consisted mainly of the sodium salt of N-carbamylphenylalanine with a small amount of 5-benzylhydantoin present.

EXAMPLE 5

5 Wt % Raney Nickel, 0 Psig 40° C., 150 Mole % NaOH

A 500 ml round bottom flask fitted as above was charged with 300 ml of deoxygenated distilled water, 30 g of benzalhydantoin, 9.5 g of NaOH (150 mole percent on benzalhydantoin) and then 1.5 g of No. 2800 Raney Nickel (Davison Div.—W. R. Grace) [5 wt % on benzalhydantoin]. After 5 hours of stirring and H₂ flow, the reduction was 53 percent complete; at 12.75 hours, 92 percent complete by UV analysis; at 19 hours, the reaction was 100 percent complete by liquid chromatography and UV analysis. The product was essentially all N-carbamylphenylalanine with a trace of 5-benzylhydantoin.

EXAMPLE 6

20 Wt % of Raney Nickel, 0 Psig, 40° C., 172 Mole % NaOH

Similar to Example 4 above except 1.8 g (172 mole percent) of NaOH was used. The reaction was done in 7 hours (over 98 percent complete based on UV analysis). Liquid chromatographic analysis showed the product to consist of 47.8 percent 5-benzylhydantoin, 50.2 percent N-carbamylphenylalanine, 0.3 percent phenylalanine and 1.7 percent 5-benzalhydantoin. The catalyst was then filtered off. The filtrate was now neutralized with hydrocloric acid to pH 7–8. Upon evaporation to dryness, the filtrate gave 8 g of white solid. The amount of NaCl present was determined by titration and so the yield of benzylhydantoin/N-carbamylphenylalanine was essentially quantitative. After thorough washing with water to remove salt, the remaining solid had a melting point of 188° C.–190° C.

EXAMPLE 7

5 Wt % Raney Nickel, 40 Psig, 25° C., 200 Mole % NaOH

Similar to example 1 above except a 500 ml Parr pressure bottle was used. 30 g of benzalhydantoin, 300 ml of distilled water, 12.7 g of NaOH and 1.5 g No. 2800 Raney Nickel (Davison Div.—W. R. Grace) were added. After 8 hours of hydrogenation, the reaction was 92 percent complete based on UV analysis and 100 percent complete after 10 hours. Liquid chromatographic analysis showed 0.8 percent phenylalanine, 92.0 percent N-carbamylphenylalanine, 2.3 percent 5-benzylhydantoin, 1.3 percent phenylpyruvic acid and 1.6 percent benzalhydantoin, all present as the sodium salts.

EXAMPLE 8

5 Wt % Raney Nickel, 0 Psig 40° C., 200 Mole % NaOH

Same as example 7 except a 500 ml round bottom flask was used and the H₂ was added at atmospheric pressure. After 7 hours, the reaction was 76 percent complete; at 14.5 hours, over 95 percent complete based on UV analysis.

EXAMPLE 9

5 Wt % of Raney Nickel, 0 Psig 50° C.–80° C., 150 Mole % of NaOH

Similar to Example 8 except for the higher temperature. The reaction was 100 percent complete in 15–16 hours based on UV analysis. The product contained 9 percent phenylpyruvic acid and 4 percent phenylacetic acid as the sodium salts.

The above Examples can be summarized in the following table:

| Example No. | % Catalyst | % NaOH | Reaction Time Hr. | % Hydrogenation |
|---|---|---|---|---|
| 1 | 20 | 0 | 53.5 | 91% |
| 2 | 30 | 0 | 45 | 95% |
| 3 | 20 | 100 | 23 | 95% |
| 4 | 20 | 113 | 8 | >95% |
| 5 | 5 | 150 | 12.75 | 92% |
| 6 | 20 | 172 | 7 | 98% |
| 7 | 5 | 200 | 8 | 92% |
| 7 | 5 | 200 | 10 | 100% |
| 8 | 5 | 200 | 14.5 | >95% |
| 9 | 5 | 200 | 15–16 | 100% |

Thus, the Examples illustrate the surprising feature of this invention. At high levels of catalyst usage, 20–30 percent by weight based on benzalhydantoin, and 0–100 mole percent NaOH based on 5-benzalhydantoin (Examples 1–3), reaction (hydrogenation) times of 23–53.5 hours are needed to obtain over 90 percent hydrogenation. With over 100 mole percent NaOH, as little as 5 percent catalyst will give >90 percent hydrogenation in only 13–15 hours (Examples 5, 7, 8 and 9). With the 20 percent catalyst level used in Examples 1–3, >90 percent hydrogenation is observed in 7–8 hours if over 100 mole percent NaOH is added to the mixture (Examples 4 and 6). In fact, as little as 1–2 percent catalyst can be used provided that >100 mole percent of NaOH is present. Even at these low levels of catalyst, >90 percent hydrogenation can be observed in 26–50 hours. These reaction times are typical of the time needed to attain >90 percent hydrogenation with 20–30 percent catalyst and 0–100 mole percent NaOH as illustrated in Examples 1–3.

EXAMPLE 10

This Example demonstrates the reduced frothing or foaming achieved by the present invention.

A 500 milliliter round-bottom flask equipped with stirrer, thermometer, condenser, $H_2$ gas inlet tube and heating mantle was charged with 300 milliliters deoxygenated water and 12.95 grams 98.6 percent NaOH. The temperature was raised to 50° C. After the NaOH was dissolved, 15 grams of 5-benzalhydantoin was added followed by 3 grams of Raney nickel No. 2800 (Davison Div.—W. R. Grace). Hydrogen gas was passed in for 30 minutes at 50° C. No foaming or frothing was evident and most of the insoluble sodium salt of benzalhydantoin dissolved. Then 15 grams more of benzalhydantoin was added under hydrogen and again no foaming or frothing occurred. After 60 minutes more at 50° C., the remaining 30 grams of benzalhydantoin was added. Still no foaming or frothing occurred. The hydrogenation was complete in less than 15 hours additional reaction time.

EXAMPLE 11

Example 10 was repeated except that a 22 liter (5 gallon) round-bottom flask was used with larger quantities of chemicals: 649 grams of 98.6 percent pure NaOH, 3,000 grams of benzalhydantoin added in 750 gram, 750 gram and 1,500 gram portions at the start, after 30 minutes and after another 30 minutes, respectively, 12 liters of deoxygenated distilled water and 150 grams No. 2800 Raney nickel. No foaming or frothing occurred during the hydrogenation carried out at 50° C.

EXAMPLE 12

13.6 kilograms (30 pounds) of a wet filter cake of benzalhydantoin at 96 percent purity on a dry basis was charged to a reactor along with 83.3 liters (22 gallons) of distilled water. The reactor agitator was turned on slow and a slight nitrogen purge was begun. 2.27 kilograms (5 pounds) of sodium hydroxide pellets were added to the reactor. 1.36 kilograms (3 pounds) of No. 2800 Raney nickel and 0.91 kilograms (2 pounds) of No. 3100 Raney nickel were added to the reactor over a period of about 10 minutes. The nitrogen purge was ceased and 0.34 Bar gauge (5 psig) hydrogen was introduced into the reactor. The reactor temperature was 20° C. (68° F.). 70 grams of triethylamine was added to the reactor and the hydrogen pressure was increased to 0.55 Bar gauge (8 psig). Heating via the reactor water jacket was started. The hydrogen pressure was then increased to 0.69 Bar gauge (10 psig) with the agitator speed increased to 200 rpm. Foaming had subsided considerably. The reactor temperature was maintained at 40°–45° C. The reaction was continued until 3 hours after the initial addition of the benzalhydantoin. The hydrogen pressure in the reactor was then reduced to 0.14 Bar gauge (2 psig) and 2.27 kilograms (5 pounds) of sodium hydroxide pellets and 13.6 kilograms (30 pounds) of benzalhydantoin wet cake was added. The reactor was pressured to about 4 kilograms (9 pounds) and the agitator speed was increased to 250 rpm. The temperature of the reactor was 45° C. (113° F.). After about 24 hours further reaction or 28 hours complete reaction time, the heat in the jacket was reduced and the agitator was shut off. After cooling the reactor, the Raney nickel catalyst was drained from the bottom of the reactor and the hydrogen flow was ceased. About 3 gallons of black solution containing catalyst was collected. The remainder of the liquid from the reactor was filtered through a Buchner funnel and about 125 liters (33 gallons) of filtrate was collected. A 20 hour sample showed 100 percent hydrogenation by liquid chromatography. No foaming or frothing was noted during the reaction.

EXAMPLE 13

The process of Example 12 was repeated using initially 57 liters (15 gallons) distilled water and 14.5 kilograms (32 pounds) of freshly prepared washed benzalhydantoin wet cake. After standing overnight under low agitation and low nitrogen purge, 26.5 liters (7 gallons) additional water was added to the reactor. 2.27 kilograms (5 pounds) of sodium hydroxide pellets were added, the reactor temperature being 30° C. 2.27 kilograms (5 pounds) of No. 2400 Raney nickel catalyst followed by 70 grams triethlamine were added to the reactor. Hydrogen was introduced into the reactor which was pressurized to 0.62 Bar gauge (9 psig) at a reactor temperature of 37° C. and agitator speed of 200 rpm. Two hours after the pressurization of the reactor with $H_2$, an additional 2.27 kilograms (5 pounds) sodium hydroxide pellets and approximately 13.6 kilograms (30 pounds) of benzalhydantoin washed wet filter cake was added. The reaction product was sampled after 9 hours and 12.5 hours. After 9 hours the reaction was 88 percent complete and after 12.5 hours the reaction was 96 percent benzylhydantoin. No foaming or frothing was noted during the reaction.

Additional features of the preferred and most preferred features of the invention are found in the claims hereinafter.

What is claimed is:

1. A process for the production of a saturated hydantoin and/or ring opened hydantoin derivative thereof from an unsaturated hydantoin which comprises the step of accomplishing the hydrogenation of said hydantoin and/or hydantoin derivative in an aqueous reaction mixture containing a Raney nickel catalyst in the presence of more than a stoichiometric amount of caustic, wherein said hydantoin and/or hydantoin derivative is present in a amount relative to the water sufficient to cause frothing and foaming and is incrementally added to said aqueous mixture in an amount sufficient to avoid foaming.

2. The process of claim 1 wherein the amount of caustic ranges from about 100 to about 300 mole percent based on the amount of unsaturated hydantoin.

3. The process of claim 1 wherein the amount of caustic ranges from about 105 to about 200 mole percent based on the amount of unsaturated hydantoin.

4. The process of claim 2 wherein the amount of Raney nickel catalyst ranges from about 0.3 percent to about 50 percent based on weight of the unsaturated hydantoin.

5. The process of claim 1 wherein the unsaturated hydantoin to be reduced has the formula:

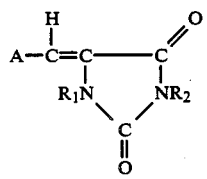

wherein A is X and X is unbranched or branched alkyl or alkenyl, cycloalkyl, cycloalkenyl, alkylthio, hydroxyalkyl, haloalkyl, haloalkenyl, aralkyl, mono or dialkylaminoalkyl, acylaminoalkyl, mercaptoalkyl, cycloalkyl having a —CH$_2$— group replaced by —O—, —S—, or —NH—, cycloalkenyl having a —CH= replaced by —O—, —S—, or —N=;

$R_1$ and $R_2$ are the same or different and are hydrogen, alkyl, aryl, acyl or amino.

6. The process of claim 1 wherein the unsaturated hydantoin to be reduced has the formula:

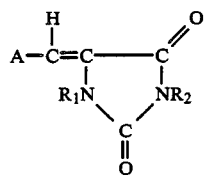

wherein A is Y and Y is

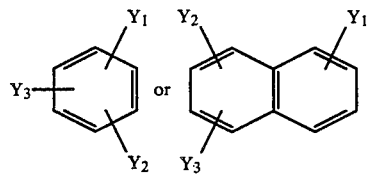

wherein $Y_1$, $Y_2$ and $Y_3$ are the same or different and are hydrogen, alkyl, alkenyl, cycloalkyl, cycloalkenyl, aryl, halogen, hydroxy, nitro, cyano, amino, alkylaminoalkyl, dialkylaminoalkyl, alkoxy, alkylthio, acyloxy, haloalkyl, haloalkenyl, hydroxyalkyl, mercaptoalkyl, alkaryl, aralkyl, acylaminoalkyl, cycloalkyl having a —CH$_2$— group replaced by —O—, —S—, or —NH— cycloalkenyl having a —CH= replaced by —N= or where two of the members, $Y_1$, $Y_2$, and $Y_3$ are joined together to form an alkylene group having at least one —CH$_2$— group replaced by —O—, —S—, or —NH— or an alkenylene group having at least one —CH= group replaced by —N=;

$R_1$ and $R_2$ are the same or different and are hydrogen, alkyl, aryl, acyl or amino.

7. The process of claim 6 wherein the unsaturated hydantoin is 5-benzalhydantoin.

8. The process of claim 1 wherein said hydantoin or hydantoin derivative is used in an amount above about 10 percent based on the weight of the water.

9. The process as recited in claim 1 wherein the incremental addition is conducted using fractions of the charge of hydantoin ranging up to ½ of the charge per addition.

* * * * *